(12) United States Patent
Cattaneo et al.

(10) Patent No.: US 9,138,334 B2
(45) Date of Patent: Sep. 22, 2015

(54) MEDICAL DEVICE

(71) Applicant: ACANDIS GmbH & Co. KG, Pfinztal (DE)

(72) Inventors: Giorgio Cattaneo, Karlsruhe (DE); Frank Nagl, Karlsruhe (DE); Werner Mailaender, Engelsbrand Grunbach (DE)

(73) Assignee: ACANDIS GMBH & CO. KG, Pfinztal (DE)

( * ) Notice: Subject to any disclaimer, the term of this patent is extended or adjusted under 35 U.S.C. 154(b) by 0 days.

(21) Appl. No.: 13/768,886

(22) Filed: Feb. 15, 2013

(65) Prior Publication Data

US 2013/0218254 A1    Aug. 22, 2013

(30) Foreign Application Priority Data

Feb. 17, 2012   (DE) .......................... 10 2012 101 294

(51) Int. Cl.
A61F 2/82     (2013.01)
A61F 2/88     (2006.01)
A61F 2/91     (2013.01)
A61F 13/00    (2006.01)

(52) U.S. Cl.
CPC . A61F 2/82 (2013.01); A61F 2/885 (2013.01); A61F 2/91 (2013.01); A61F 13/00008 (2013.01); A61F 13/00029 (2013.01)

(58) Field of Classification Search
CPC ... A61F 2/82; A61F 2/885; A61F 2250/0014; A61F 2250/0018; A61F 2250/0028; A61F 2250/0029; A61F 2250/0036; A61F 2250/0037; A61F 2/04; A61F 2/06; A61F 2/07; A61F 2/90
USPC .................. 623/1.2, 1.15, 1.16, 1.22, 1.53
See application file for complete search history.

(56) References Cited

U.S. PATENT DOCUMENTS

| 5,514,154 | A | 5/1996 | Lau et al. | |
| 5,968,088 | A | 10/1999 | Hansen et al. | |
| 6,042,597 | A | 3/2000 | Kveen et al. | |
| 2010/0004735 | A1* | 1/2010 | Yang et al. | 623/1.16 |
| 2010/0131045 | A1* | 5/2010 | Globerman et al. | 623/1.16 |
| 2013/0197623 | A1* | 8/2013 | McHugo | 623/1.18 |

FOREIGN PATENT DOCUMENTS

| DE | 699 34 244 T2 | 5/2000 |
| DE | 601 32 603 T2 | 8/2002 |
| EP | 1 970 032 A2 | 9/2008 |

* cited by examiner

Primary Examiner — Randy Shay
Assistant Examiner — Dinah Baria
(74) Attorney, Agent, or Firm — Brooks Kushman P.C.

(57) ABSTRACT

A medical device with a radially compressible and expandable lattice structure (10) contains at least one closed cell (15) delimited in each case by four webs (11, 12, 13, 14) coupled to one another in one piece, of which at least one web (11, 12, 13, 14) is embodied as a stabilisation web (11, 13) with a first web width $b_1$ and at least two further webs (11, 12, 13, 14) are embodied as connecting webs (12, 14) with a second web width $b_2$, wherein the connecting webs (12, 14) are arranged inside the cell (15) so that they lie parallel opposite one another and are connected to one another by the stabilisation webs (11, 13) and wherein the ratio $b_1/b_2$ between the first web width $b_1$ and the second web width $b_2$ is at least 1.2.

15 Claims, 2 Drawing Sheets

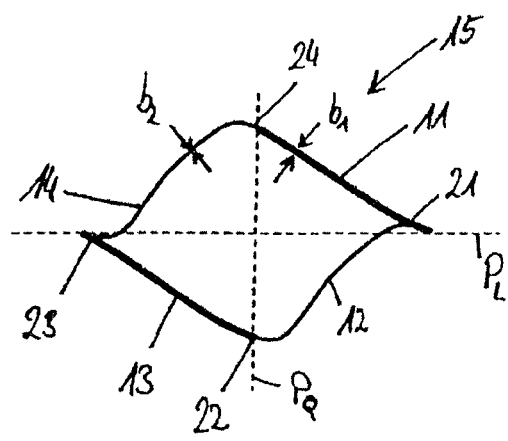
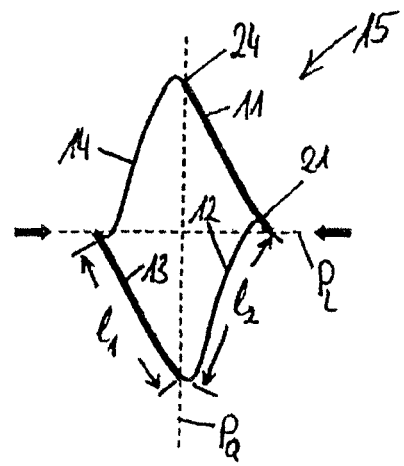
Fig. 1a  Fig. 1b
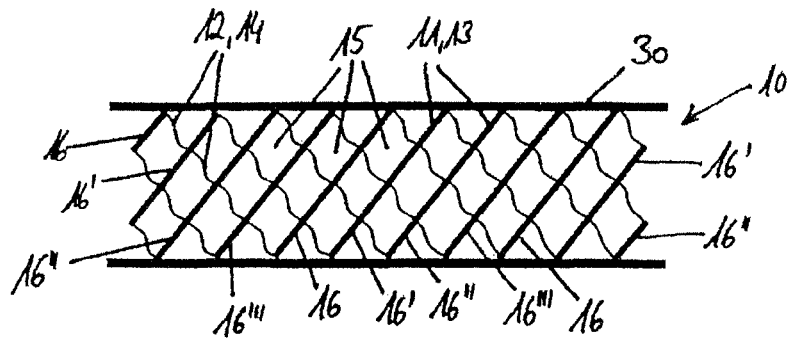
Fig. 2a
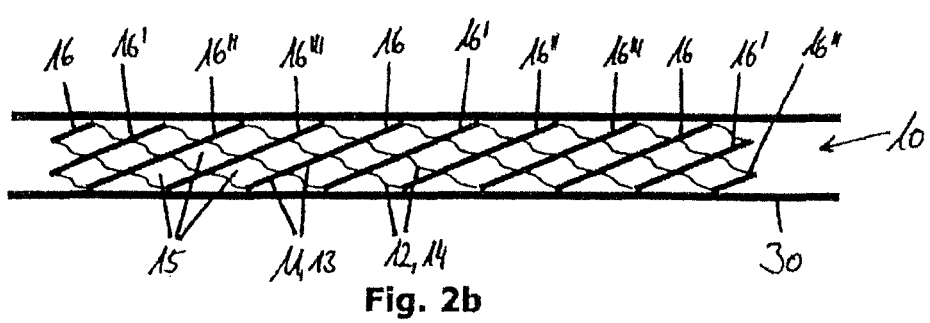
Fig. 2b

MEDICAL DEVICE

CROSS-REFERENCE TO RELATED APPLICATIONS

This application claims priority to German Patent Application No. 10 2012 101 294.6 filed Feb. 17, 2012 which is herein incorporated by reference.

BACKGROUND OF THE INVENTION

1. Field of the Invention

The invention relates to a medical device comprising a radially compressible and expandable lattice structure. Devices of this kind are known from practice, for example, in the form of stents or emboli traps.

2. Background Art

Known stents comprise a lattice structure, which is formed from cells. The cells are delimited by interconnected webs. In particular, stents are known that are cut from tubes, for example, by laser cutting.

Stents are generally radially compressible and expandable. For introduction into a blood vessel, the stent is guided via a catheter in a compressed state. After leaving the catheter, the stent opens up or expands and adapts itself to the vessel wall. At the same time, the stent attempts to adopt a circular cylindrical shape. In other words, the stent expands radially uniformly.

The radially uniform expansion of the stent is comparatively unproblematic in straight blood vessels. However, it has been found that when stents are used in curved blood vessels, forces develop that can impede uniform radial expansion of the stent. In particular, the stent expands more strongly in the transverse direction, i.e. parallel to the axis of curvature of the blood vessel, than in a direction perpendicular to the axis of curvature of the blood vessel. In other words, in vessel curvatures, a substantially oval cross-sectional profile of the stent is established. Therefore, there is a risk of the stent exerting different radial forces on some sections of the vessel wall. This can result in additional local irritation of the vessel walls. There is also a risk of gaps forming between the lattice structure of the stent and the blood vessel in some sections. Since, the lattice structure influences the blood flow in the region between the lattice structure and the blood-vessel wall, this can result in the formation of blood clots.

SUMMARY OF THE INVENTION

An object of the invention is to provide a medical device facilitating good adaptation to a vessel wall, in particular in curved hollow body organs. These and other objects are achieved by a medical device comprising a radially compressible and expandable lattice structure, including at least one closed cell delimited by four webs coupled to one another in one piece, of which at least one web is a stabilisation web with a first web width $b_1$ and at least two further webs are connecting webs with a second web width $b_2$, wherein the connecting webs are arranged inside the cell so that they lie parallel opposite one another and are connected to one another by a stabilisation web and wherein the ratio $b_1/b_2$ between the first web width $b_1$ and the second web width $b_2$ is at least 1.2.

BRIEF DESCRIPTION OF THE DRAWINGS

The invention will now be explained in more detail in the following with reference to exemplary embodiments and with reference to the attached schematic drawings, which show:

FIG. 1a: a top view of a cell of the lattice structure of a medical device according to a preferred exemplary embodiment of the invention in the resting state;

FIG. 1b: the cell according to FIG. 1a on exposure to axial compression forces;

FIG. 2a: a side view of the lattice structure of a medical device according to a further preferred exemplary embodiment of the invention in an implanted state in a hollow organ of a body with a relatively large cross-sectional diameter;

FIG. 2b: the lattice structure according to FIG. 2a in an implanted state in a hollow region of the body with a relatively small cross-sectional diameter;

DETAILED DESCRIPTION OF THE PREFERRED EMBODIMENT(S)

Figure 3:
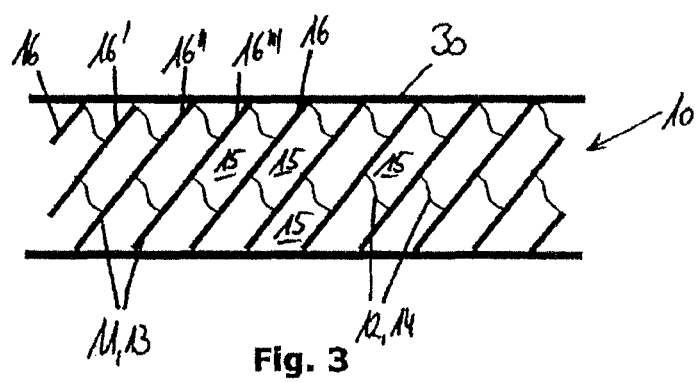
FIG. 3: a side view of the lattice structure of a medical device according to a further preferred exemplary embodiment of the invention in an implanted state, wherein the connecting webs have a greater web length than the stabilisation webs.

The invention is thus directed to a medical device comprising a radially compressible and expandable lattice structure comprising at least one closed cell. The closed cell in each case is delimited by four webs coupled to one another in one piece. At least one of the webs is embodied as a stabilisation web with a first web width $b_1$. At least two further webs are embodied as connecting webs with a second web width $b_2$. The connecting webs are arranged inside the cell so that they lie parallel opposite one another and are connected to one another by the stabilisation web. The ratio $b_1/b_2$ between the first web width $b_1$ and the second web width $b_2$ is at least 1.2.

The invention is based on the idea of embodying at least two webs of a cell of the lattice structure wider than two other webs. At the same time, the lattice structure can have a uniform wall thickness. In other words, all webs of the cell have the same web thickness, wherein the web thickness should be measured in the radial direction relative to the longitudinal axis of the lattice structure.

The invention explicitly relates to a medical device with a lattice structure comprising closed cells (closed cell design). This means that each web of a cell is connected at each of its longitudinal ends with at least two further webs, in particular at least one web of the same cell and one web of an adjacent cell. In a lattice structure with closed cells, all webs are coupled to connectors, which connect the webs of a plurality of cells to one another. Contrary to this, lattice structures with open cells (open cell design) comprise webs, which are connected to one another inside a cell and comprise a terminal connector freely arranged in the cell. The lattice structure with the medical device according to the invention preferably has no terminal connectors or has at least one cell with no terminal connector, i.e. one closed cell.

With the medical device according to the invention, in principle the possibility is not excluded that, for example, holding elements inside a closed cell are arranged at the axial ends of the lattice structure comprising the two interconnected webs, wherein the connection point between the two webs is freely arranged in the cell. The purpose of the holding elements can be, when placed in a blood vessel, in particular in a curved blood vessel, to lift themselves out of the wall plane of the lattice structure. The enables the lattice structure to be securely anchored in a blood vessel. Insofar, with the medical device according to the invention, it is quite possible for the lattice structure to comprise different cells, in particular to be formed partially by closed cells and partially by closed cells with holding elements. In general, it is advantageous for the entire lattice structure to be embodied as one piece or one part. This can, for example, be ensured by producing the lattice structure from a full tube. In particular, the lattice structure can be produced by laser cutting.

The formation of the lattice structure by to a large extent closed cells—which includes closed cells with holding elements—has the advantage that, after a partial discharge from a catheter or a guide system generally, the lattice structure can be withdrawn back into the catheter or the guide system. Since the cells are closed, no protruding, in particular free, terminal connectors can become caught during the withdrawal. In the case of closed cells comprising holding elements, the holding elements are preferably aligned such that the tips formed by the two interconnected webs of the holding elements point in the distal direction relative to the guide system. This prevents the holding element from being pushed over the catheter wall on the withdrawal of the lattice structure into a catheter and blocking further withdrawal.

With the invention, the different web widths of the webs inside the closed cell increase the flexibility of the lattice structure overall. This is particularly evident on the expansion of the lattice structure in a curved hollow organ of a body. When the lattice structure is arranged in a curved hollow organ of a body, the wall region, which lies closer to the curvature mid-point of the hollow organ of the body than an opposite wall section, is relatively more greatly curved. This results in an axial compression of the cells in the more greatly curved wall region of the lattice structure. The bending flexibility of the lattice structure is decisive for ensuring good contact between the lattice structure and the vessel wall. With the invention, the bending flexibility is increased by the different web widths between the stabilisation webs and the connecting webs. To this end, it is preferably provided that, at least in the wall region, which, with the arrangement of the lattice structure in a curved hollow organ of a body, is more greatly bent than other wall regions, the lattice structure comprises cells formed from stabilisation webs and connecting webs. The relatively narrower connecting webs are more greatly deformed on the compression or axial compression of the lattice structure or a wall region of the lattice structure than the relatively wide stabilisation webs. Additionally, the relatively narrower connecting webs can be subject to more torsion than the relatively wider stabilisation webs, i.e. they can become twisted. The result of this is that the lattice structure has a higher flexibility overall than lattice structures with closed cells, the webs of which have a uniform width.

The different web widths between the stabilisation webs and the connecting webs can, on the one hand, serve to adjust the radial force of the lattice structure and, on the other hand, to ensure increased flexibility. The stabilisation webs endow the lattice structure with the necessary stability and radial force to support a blood vessel. On the other hand, the connecting webs have a smaller web width in order to ensure increased flexibility, in particular bending flexibility, of the lattice structure. A ratio between the first web width of the stabilisation webs and the second web width of the connecting webs of at least 1.2 has been found to be particularly suitable in order, on the one hand, to ensure sufficient vessel support and, on the other hand, to offer high flexibility, in particular bending flexibility.

In general, it can be provided that, in a resting state, i.e. in a completely expanded state, the lattice structure adopts a circular-cylindrical or tubular shape, without the influence of external forces.

In a preferred embodiment of the medical device, it is provided that the ratio between the first web width $b_1$ and the second web width $b_2$ is at least 1.5, and in order of increasing preference, at least 1.8, at least 2, at least 2.5, at least 3, at least 4, at least 5, at least 6, at least 8, at least 10, and at least 12.

In order to form a symmetrical cell, in preferred way, at least two stabilisation webs are provided. Of the four webs of a cell, therefore, two webs can be embodied as stabilisation webs with the first web width $b_1$. The two other webs form the connecting webs with the second web width $b_2$. The cell is preferably delimited alternately by stabilisation webs and connecting webs, i.e. the stabilisation webs provide a connection between the connecting webs. The stabilisation webs and the connecting webs can in each case be arranged so that they lie parallel opposite one another.

It can also be provided that the lattice structure comprises a plurality of adjacent closed cells, the stabilisation webs of which are connected to one another in alignment so that at least one row of stabilisation webs is formed, which winds in a helical shape about a longitudinal axis of the lattice structure. In other words, the row of stabilisation webs can adopt the shape of a helical spring, in particular a wound torsion spring. The row of stabilisation webs is here formed by stabilisation webs arranged in alignment to one another and directly connected to one another. This achieves particularly high bending flexibility of the lattice structure, in particular over the entire length of the lattice structure.

Preferably, at least two rows of stabilisation webs are formed, which are connected to one another by the connecting webs. The connecting webs can be arranged at regular intervals between two rows of stabilisation webs in order to ensure uniform, flexible behaviour of the lattice structure.

A contribution is made to uniform flexibility in at least one section of the lattice structure if the connecting webs of adjacent closed cells are arranged in parallel to one another. Therefore, the connecting webs of adjacent closed cells can have the same angle or the same orientation relative to the longitudinal axis of the lattice structure.

In a further preferred embodiment, it is provided that the stabilisation webs have a substantially linear course. In this way, the shape of a row of stabilisation webs further approximates the shape of a helical spring. This contributes to improved crimpability and bending flexibility of the lattice structure.

It can also be provided that the connecting webs are embodied as substantially S-shaped. The S-shaped embodiment of the connecting webs achieves easier deformability of the connecting webs. This further improves the flexibility, in particular bending flexibility, of the lattice structure. Even with a substantially uneven shape of the connecting webs, they extend parallel to one another inside a cell. In other words, the connecting webs, preferably all connecting webs of the lattice structure, have the same course so that overall a parallel arrangement is produced. Therefore, there is a uniform distance between two connecting webs which are adjacent in the circumferential direction of the lattice structure.

Preferably, the stabilisation webs have a first web length and the connecting webs a second web length, wherein the first web length and the second web length are different. This enables the flexibility and/or bendability of the lattice structure to be adjusted for different applications.

For example, it is provided in a preferred embodiment that the ratio of the first web length to the second web length is at least 1.2, and in order of increasing preference, at least 1.5, at least 2, at least 2.5, at least 3, at least 4, and at least 5. In this embodiment, in which the stabilisation webs having the first web length are longer than the connecting webs having the second web length, it is advantageously achieved that the flexibility, in particular bending flexibility, and the crimpability of the lattice structure are increased when using the medical device in hollow body organs, in particular blood vessels, with relatively small diameters.

Alternatively, it can be provided that the ratio of the second web length to the first web length is at least 1.2, and in order of increasing preference, at least 1.5, at least 2, at least 2.5, at least 3, at least 4, and at least 5. In this embodiment, therefore, the connecting webs have a greater web length than the stabilisation webs. This reduces the fine mesh width of the lattice structure or reduces the cell size. Since the connecting webs have a relatively high capacity for deformation, the flexibility, in particular bending flexibility, of the lattice structure is hardly impaired at all. In this embodiment, the medical device is in particular suitable for influencing flow conditions in an aneurysm, i.e. for positioning in a section of a blood vessel from which an aneurysm has developed. Alternatively, the medical device can advantageously be used in the treatment of stenosis, wherein the finer mesh width prevents plaque components of the stenosis entering the blood flow.

In a preferred embodiment of the medical device according to the invention, the lattice structure comprises at the utmost 8, more preferably at the utmost 6, yet more preferably at the utmost 4, still more preferably at the utmost 3, and most preferably at the utmost 2, rows of stabilisation webs. The rows of stabilisation webs can be arranged at regular intervals around the circumference of the lattice structure. In particular, it can be provided that, in each case between two rows of stabilisation webs, a row of webs extends in a helical shape around the longitudinal axis of the lattice structure, which is formed from webs with a different, in particular smaller, web width than the stabilisation webs.

Specifically, it is provided in a preferred embodiment that the lattice structure comprises a plurality of rows of webs extending parallel to one another and winding in the same direction of winding around the longitudinal axis of the lattice structure. The row of webs are formed by webs of individual cells in alignment with one another and connected to one another, wherein the webs have a linear course. At least two of the rows of webs wound in a helical shape around the longitudinal axis of the lattice structure are formed from stabilisation webs arranged in sequence or connected to one another in alignment. Therefore, at least two of the rows of webs form rows of stabilisation webs. A plurality of rows of stabilisation webs can be provided, wherein, in a particularly preferred embodiment of the invention, the rows of stabilisation webs are arranged distributed at regular intervals around the circumference of the lattice structure. In particular, the lattice structure can be embodied as a pattern so that in each case a repeating sequence of row of webs with and without stabilisation webs is provided in the circumferential direction of the lattice structure.

In addition, it can be provided with the medical device according to the invention that, in the circumferential direction, the lattice structure has at least 6, in particular at least 8, in particular at least 12, in particular at least 18, in particular at least 24, in particular at least 32, in particular at least 36, in particular at least 48, in particular at least 56, in particular at least 64, connecting webs. The aforementioned number of connecting webs is determined in the circumferential direction, i.e. the decisive factor is the number of the connecting webs intersecting an individual cross-sectional plane of the lattice structure. The number of the connecting webs is able, on the one hand, to influence the bending flexibility of the lattice structure or the medical device generally. On the other hand, increasing the number of connecting webs simultaneously results in a finer mesh width of the lattice structure. Therefore, a high number of connecting webs, that is a finer mesh width, is expedient for medical devices, which are used, for example, to cover an aneurysm.

The number of the connecting webs of the lattice structure can be limited. In particular it can be provided that the lattice structure in circumferential direction comprises at the utmost 120, in particular at the utmost 100, in particular at the utmost 80, in particular at the utmost 70, in particular at the utmost 60, in particular at the utmost 50, connecting webs. The aforementioned upper limits, on the one hand, ensure good influence of the flow due to the very fine mesh width, for example, for the treatment of an aneurysm, and, on the other hand, ensure that the bending flexibility is still sufficient for the lattice structure to be positioned well in a curved hollow organ of a body.

To ensure the bending stability of the lattice structure that is expedient for the purposes of the invention, it is further preferable for the second web width $b_2$ to be at the utmost 35 µm, in particular at the utmost 30 µm, in particular at the utmost 25 µm, in particular at the utmost 20 µm, and in particular at the utmost 15 µm.

In addition, it has been found to be beneficial for the bending flexibility in general and the crimpability inside a guide system or catheter in particular for the stabilisation webs and the connecting webs to adopt the same angle relative to the longitudinal axis of the lattice structure, with the inverse sign in each case. This means that the bisector between a connecting web and a stabilisation web arranged adjacent in the circumferential direction and directly connected to the connecting web extends parallel to the longitudinal axis. The angle with curved, in particular S-shaped, webs is determined between the longitudinal axis, or a projection of the longitudinal axis, in the wall plane of the lattice structure and a virtual connecting line connecting the two ends of the curved webs.

It has been shown that, with reference to the figures, on the implantation of an expandable lattice structure 10 in a hollow organ of a body, in particular a blood vessel 30, with vessel curvature, the individual cells 15 of the lattice structure 10 are deformed differently in order to follow the course of the blood vessel 30. While the radially outer regions of the lattice structure 10 relative to the curvature mid-point of the blood vessel 30 or of the curved blood-vessel section are stretched, the radially internal wall sections are substantially compressed. For the individual cells 15 of the lattice structure 10, this means that cells which are arranged further away from the curvature mid-point of the blood-vessel curvature have a greater axial extension than cells 15 which are arranged in a wall section of the lattice structure 10, which is closer to the curvature mid-point of the blood-vessel curvature.

The cell 15 of the lattice structure 10 substantially comprises four webs 11, 12, 13, 14, which delimit the cell 15 or the cell surface. The four webs 11, 12, 13, 14 are connected to one another, wherein in each case a connector 21, 22, 23, 24 is arranged between two webs 11, 12, 13, 14. The connectors 21, 22, 23, 24 substantially form junctions or linkage points between two webs 11, 12, 13, 14 of a single cell 15. Simultaneously, the connectors 21, 22, 23, 24 can form junctions or linkage points to adjacent cells 15, that is overall couple more than two webs 11, 12, 13, 14 to one another, wherein at least one of the coupled webs 11, 12, 13, 14 belongs to an adjacent cell 15.

Overall four connectors 21, 22, 23, 24 are assigned to the individual cell 15. At the same time, a first connector 21 connects a first stabilisation web 11 to a first connecting web 12. A second connector 22 couples the first connecting web 12 to a second stabilisation web 13. The second stabilisation web 13 is coupled by a third connector 23 to the second connecting web 14. A fourth connector 24 connects the second connecting web 14 to the first stabilisation web 11.

FIG. 1a shows a cell 15 of a lattice structure 10 of the medical device according to the invention according to a preferred exemplary embodiment. The medical device can generally comprise a stent, an emboli trap and/or a blood filter. In a preferred way, the lattice structure 10 is embodied as a circular cylinder at least in sections. Generally, the lattice structure 10 is radially compressible and expandable. The lattice structure 10 can also a have radially compressed, i.e. crimped, state, which is suitable for guiding the lattice structure 10 in a hollow organ of a body, in particular a blood vessel 30. The lattice structure 10 can also have a radially expanded state, in which the lattice structure 10 has a greater cross-sectional diameter than in radially compressed state. The radially expanded state of the lattice structure 10 also comprises an implanted state of the lattice structure 10, wherein the lattice structure 10 exerts a radial force on the hollow body organ, in particular the blood vessel 30. A further expanded state of the lattice structure 10 relates to the resting state or as-manufactured state, in which the lattice structure 10 is free of outer forces.

Of the four webs 11, 12, 13, 14 of cell 15, in each case two opposite 11, 13, 12, 14 are embodied identically. Specifically, it is provided that the cell 15 comprises two stabilisation webs 11, 13 arranged opposite one another. The stabilisation webs 11, 13 are in particular separated from one another by two connecting webs 12, 14, wherein the connecting webs 13, 14 are also embodied identically. The stabilisation webs 11, 13 and the connecting webs 12, 14 differ from one another. It is in particular provided that the stabilisation webs 11, 13 have a first web width $b_1$ and the connecting webs 12, 14 have a second web width $b_2$. The first web width $b_1$ of the stabilisation webs 11, 13 is greater than the second web width $b_2$ of the connecting webs 12, 14. It has in particular been found to be advantageous for the first web width $b_1$ to be in a ratio to the second web width $b_2$ ($b_1/b_2$) which is at least 1.2, in particular at least 1.5, in particular at least 1.8, in particular at least 2, in particular at least 2.5, in particular at least 3, in particular at least 4, in particular at least 5, in particular at least 6.

The stabilisation webs 11, 13 substantially form a support structure of the lattice structure 10. On the other hand, the connecting webs 12, 14 provide increased flexibility of the lattice structure 10. To this end, as shown in FIG. 1a, it can advantageously be provided that the connecting webs 12, 14 are S-shaped, i.e. extend in an S-shape between the stabilisation webs 11, 13. The cell 15 according to FIG. 1a is in a force equilibrium with respect to the axial forces and the circumferential forces. This means that forces acting along the longitudinal axis of the lattice structure 10 and forces acting along the longitudinal direction of the lattice structure 10 have substantially the same value. In FIG. 1, dotted lines indicate, on the one hand, the projection $P_L$ of the longitudinal axis of the lattice structure on the wall plane of the lattice structure and, on the other hand, the projection $P_Q$ of the transverse axis of the lattice structure 10. The transverse axis corresponds to an axis of the lattice structure, which is arranged perpendicular to the longitudinal axis and extends in a cross-sectional plane of the lattice structure 10.

FIG. 1b shows the cell 15 according to FIG. 1a when axial forces act on the cell 15. This can be the case when the cell 15 is arranged in a region of the circumferential wall of the lattice structure 10, which, in implanted state inside a vessel curvature, comes to lie close to the curvature mid-point. It may be clearly identified that the cell 15 is greatly deformed, in particular in the circumferential direction, i.e. it is stretched along the projection $P_Q$ of the transverse axis. Specifically, the cell 15 is compressed in the axial direction, as indicated by the arrows in FIG. 1b, so that the second connector 22 and the fourth connector 24 in circumferential direction of the lattice structure 10 are separated from one another. Due to the different web widths, in particular the relatively smaller web width $b_2$ of the connecting webs 12, 14, the cell 15 can be slightly deformed in the axial direction so that, overall, the lattice structure 10 is able to adapt well to a vessel curvature.

FIGS. 2a to 4 described in the following show a lattice structure 10 of the medical device in a side view, wherein, for purposes of clarity, webs 11, 12, 13, 14, which are arranged on the side facing away from the observer, are not shown.

FIG. 2a shows an exemplary embodiment of the entire lattice structure 10 used in a blood vessel 30. Therefore, the lattice structure 10 is in the implanted state. The lattice structure 10 comprises a plurality of cells 15, wherein all cells 15 of the lattice structure 10 are embodied identically. In particular, each of the cells 15 in each case comprises two stabilisation webs 11, 13 and two connecting webs 12, 14. The stabilisation webs 11, 13 of adjacent cells are, on the one hand, connected to one another and, on the other, are aligned, wherein it is clearly identifiable in FIG. 2a that the stabilisation webs 11, 13 have a linear course. Therefore, the stabilisation webs 11, 13 extend in each case in a straight line between two connectors 21, 22, 23, 24. This results in rows of stabilisation webs 16, 16', 16", 16''' extending parallel to one another, wherein in the exemplary embodiment according to FIG. 2a, all webs extending in the same direction of winding around the longitudinal axis of the lattice structure 10 form stabilisation webs 11, 13, that is rows of stabilisation webs 16, 16', 16", 16'''. In the figures, the superscript identifies the number of the rows of stabilisation webs 16, 16,', 16", 16''' in order to elucidate the helical course of the rows of stabilisation webs 16, 16,', 16", 16'''. For example, with the exemplary embodiments according to FIGS. 2a to 4, it is provided that the lattice structure 10 overall comprises four rows of stabilisation webs 16, 16', 16", 16''' which are wound substantially parallel to one another in a helical shape around the longitudinal axis of the lattice structure.

It is also possible for the lattice structure 10 to comprise only one single row of stabilisation webs 16 or for the rows of stabilisation webs 16 to be formed in each case by stabilisation webs 11, 13, which in each case belong to different cells 15. In other words, the cells 15 which are arranged along a row of stabilisation webs 16 can in each case comprise only one stabilisation web 11 with the first web width $b_1$, which forms the row of stabilisation webs 16. The three other webs of the cell 15 can have other, in particular smaller, web widths. The two webs of the cell 15 connected directly to the stabilisation web 11 form the connecting webs 12, 14 with the second web width $b_2$. The web of the cell 15 opposite the stabilisation webs 11 can also have the second web width $b_2$, or any web width different from the first web width $b_1$.

In general, the row of stabilisation webs 16 extends in a helical shape, in particular similar to a helical spring, around the longitudinal axis of the lattice structure 10. If the cells 15, the webs of which form the row of stabilisation webs 16, comprise in each case two stabilisation webs 11, 13, two rows of stabilisation webs 16 extending parallel to one another are formed. The connecting webs 12, 14 of the cells 15 are arranged between the rows of stabilisation webs 16 extending parallel to one another (FIGS. 2a to 4). The connecting webs 12, 14 have an S-shaped course. The rows of stabilisation webs 16, which could be considered to be helical springs, are, therefore, held in shape by the connecting webs 12, 14. In other words, the connecting webs 12, 14 prevent the rows of stabilisation webs 16 or helical springs from expanding in an uncontrolled manner, i.e. from moving away from one another in a non-uniform manner.

FIG. 2b shows the same lattice structure 10 in implanted state in a blood vessel 30 with a relatively smaller cross-sectional diameter. Although the blood vessel according to FIG. 2b runs in a straight line, that is does not have any vessel curvature, the high flexibility of the lattice structure 10 is clearly identifiable. The rows of stabilisation webs 16 wound in a helical shape have a flatter angle to the vessel wall of the blood vessel 30 than in the exemplary embodiment according to FIG. 2a. From this it may be derived that the inclination of the rows of stabilisation webs 16 enables a relatively high ratio to be achieved between a completely compressed cross-sectional diameter and a completely expanded cross-sectional diameter of the lattice structure 10. This also applies to individual sections of the lattice structure 10, for example, a wall region, which, in implanted state of the lattice structure 10, is arranged closer to curvature mid-point of a vessel curvature than a radially opposite wall region.

FIG. 3 shows a similar lattice structure 10 of a medical device according to a preferred exemplary embodiment, wherein the stabilisation webs 11, 13 of the individual cells 15 form helical springs arranged in a helical shape. The stabilisation webs 11, 13 in each case have a linear course. However, it is generally applicable that the stabilisation webs 11, 13 can also have a curved shape, for example, an S-shape.

In the previous exemplary embodiment according to FIGS. 2a and 2b, the stabilisation webs 11, 13 and the connecting webs 12, 14 in each case have the same web length. On the other hand, in the exemplary embodiment according to FIGS. 3 and 4, it is provided that the stabilisation webs 11, 13 have a first web length $l_1$ and the connecting webs 12, 14 a second web length $l_2$, wherein the first web length $l_1$ and the second web length $l_2$ are different.

FIG. 3 shows a lattice structure 10, the connecting webs 12, 14 of which have a second web length $l_2$ which is greater than the first web length $l_1$ of the stabilisation webs 11, 13. This provides a lattice structure 10 characterised by an increased fine mesh width and is, for example, suitable for covering aneurysms.

Preferably, the ratio $(l_2/l_1)$ between the second web length $l_2$ and the first web length $l_1$ is at least 1.2, in particular at least 1.5, in particular at least 2, in particular at least 2.5, in particular at least 3, in particular at least 4, in particular at least 5.

Figure 4:
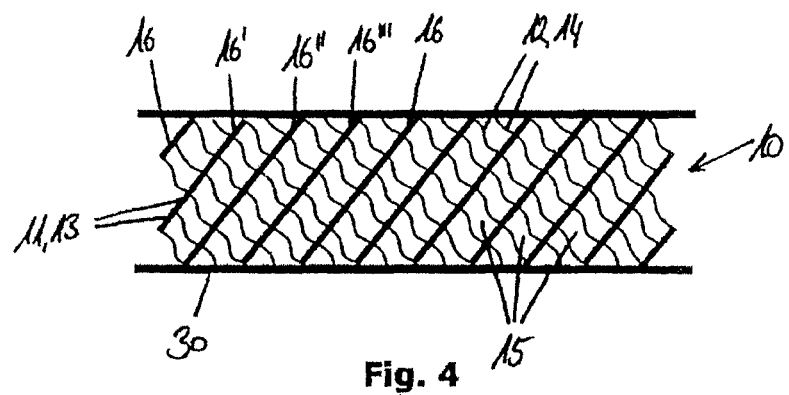
FIG. 4: a side view of the lattice structure of a medical device according to a further preferred exemplary embodiment of the invention in an implanted state, wherein the stabilisation webs have a greater web length than the connecting webs.

It is also identifiable in FIG. 3 that, in the longitudinal direction of the lattice structure 10 of adjacent cells 15, unlike the case in the exemplary embodiments according to FIGS. 2a, 2b and 4, the connecting webs 12, 14 are arranged offset to one another. The connecting webs 12, 14 of adjacent cells 15 are coupled to one another indirectly by the stabilisation webs 11, 13. Alternatively, the connecting webs 12, 14 can be arranged such that in each case two connecting webs 12, 14 are connected in alignment with one another in the longitudinal direction of adjacent cells 15, preferably similarly to the aligned connection of the stabilisation webs 11, 13. Nevertheless, the ratio $l_1/l_2$ the web lengths between the stabilisation webs 11, 13 and the connecting webs 12, 14 can at the same time still be greater than 1, in particular it can adopt one of the values named above.

In the exemplary embodiment according to FIG. 4, it is provided that the stabilisation webs 11, 13 comprise a first web length $l_1$, which is higher than the second web length $l_2$ of the connecting webs 12, 14. This provides a lattice structure 10 with flexibility and crimpability set such that the lattice structure 10 is well suited for implantation in small blood vessels 30, i.e. in blood vessels 30 with a small cross-sectional diameter. In this exemplary embodiment, it is particularly advantageous for the ratio $(l_1/l_2)$ of the first web length $l_1$ of the stabilisation webs 11, 13 and the second web length $l_2$ of the connecting webs 12, 14 to be at least 1.2, in particular at least 1.5, in particular at least 2, in particular at least 2.5, in particular at least 3, in particular at least 4, in particular at least 5.

The flexibility of the lattice structure 10 can additionally be influenced by a suitable selection of the angle between two adjacent webs 11, 12, 13, 14 of the cell 15 in the circumferential direction. The angle between two adjacent webs 11, 12, 13, 14 in the circumferential direction, for example, the first stabilisation web 11 and the first connecting web 12 or the second stabilisation web 13 and the second connecting web 14 is designated the tip angle. The tip angle is preferably at least 60°, in particular at least 70°, in particular at least 80°, in particular at least 90°, in particular at least 100°, in particular at least 110°, in particular at least 120°, in particular at least 130°, in particular at least 140°. This applies to all exemplary embodiments. In principle, it is preferable for the bisector of the tip angle to extend parallel to the longitudinal axis of the lattice structure, in particular to correspond to the projection $P_L$ the longitudinal axis.

In addition, it applies to all exemplary embodiments that the wall thickness of the lattice structure 10 is preferably uniform. Therefore, all webs 11, 12, 13, 14 of the lattice structure 10, in particular all webs 11, 12, 13, 14 of the cell 15, have the same wall thickness or web thickness. This is preferably at the utmost 90 µm, in particular at the utmost 80 µm, in particular at the utmost 70 µm, in particular at the utmost 60 µm, in particular at the utmost 50 µm, in particular at the utmost 40 µm.

Generally, the cross-sectional diameter of the lattice structure 10 in resting state or as-manufactured state can be at the utmost 12 mm, in particular at the utmost 8 mm, in particular at the utmost 6 mm, in particular at the utmost 5 mm, in particular at the utmost 4 mm, in particular at the utmost 3.5 mm, in particular at the utmost 3 mm, in particular at the utmost 2.5 mm.

The medical device according to the invention can be embodied as a stent. In this case, the lattice structure 10 preferably comprises two axial, open ends. Alternatively, it can be provided that the lattice structure 10 is connected to a transport wire and in particular comprises a closed axial end. At the same time, the medical device according to the invention can form a recanalisation device, in particular a thrombus removal system, specifically a emboli trap and/or blood filter.

Generally, the medical device according to the invention can comprise a covering, in particular a plastic covering. Polyurethane can be used as the preferred material for the covering. The covering spans the lattice structure 10, in particular the cells 15. For example, a stent graft can be formed. The covering can be substantially fluid-tight. It is also possible for the covering to have openings, in particular pores, so that the covering is at least partially permeable to fluid. The lattice structure 10 spanned by the covering is in particular suitable for the use of blood filters and/or flow diverters.

In general, it is provided with the invention that the lattice structure comprises at least one closed cell, which in each case is delimited by four webs coupled to one another in one piece, of which at least one web 11, 12, 13, 14 is embodied as a stabilisation web 11, 13 and at least two further webs 11, 12, 13, 14 are embodied as connecting webs 12, 14. In the context of the application, a closed cell 15 designates a cell which is completely embedded in the lattice structure. This means that all webs 11, 12, 13, 14 of the cell 15 are connected to at least one web 11, 12, 13, 14 of an adjacent cell. Therefore, the connectors 21, 22, 23, 24 of the cell 15 not only couple two webs 11, 12, 13, 14 of a first cell 15, but also connect these webs 11, 12, 13, 15 to at least one further web 11, 12, 13, 14 of an adjacent, second cell 15. In particular with respect to the stabilisation webs 11, 13, it is provided that each stabilisation web 11, 13 of a closed cell 15 is connected in alignment to at least one stabilisation web 11, 13 of an adjacent cell 15. Therefore, the lattice structure 10 comprises at least two rows of stabilisation webs 16 arranged in a helical shape, which extend the substantially parallel to one another. In other words, the lattice structure 10 can be formed by a plurality of helical springs extending in parallel, which are formed by the stabilisation webs 11, 13, wherein the individual helical springs are coupled to one another by the connecting webs 12, 14. At the same time, the stabilisation webs 11, 13 and the connecting webs 12, 14 are preferably connected to one another in one piece or in one part. The entire lattice structure is embodied as a single part.

With respect to the dimensions of the medical device according to the invention, in particular the lattice structure 10, the following is provided:

With a diameter of the lattice structure 10 in the as-manufactured state, that is in resting state without the application of forces, of between 6 mm and 12 mm, the internal diameter of a guide system for the lattice structure 10 or the medical device is preferably at the utmost 2.2 mm, in particular at the utmost 2 mm, in particular at the utmost 1.8 mm, in particular at the utmost 1.6 mm, in particular at the utmost 1.4 mm, in particular at the utmost 1.2 mm. In this case, it is preferably provided that the lattice structure comprises 10 connecting webs, preferably at least 12, in particular at least 18, in particular at least 24, in particular at least 32, in particular at least 36, in particular at least 48, in particular at least 56, and in particular at least 64 connecting webs 12, 14. With this variant, the maximum number of connecting webs 12, 14 is preferably at the utmost 120, in particular at the utmost 100, in particular at the utmost 80, in particular at the utmost 70.

With a diameter of the lattice structure 10 in the resting state of 2 mm to 6 mm, preferably a guide system is used with an internal diameter of at the utmost 1.0 mm, in particular at the utmost 0.72 mm, in particular at the utmost 0.6 mm, in particular at the utmost 0.51 mm, in particular at the utmost 0.42 mm. The lattice structure 10 can in this case comprise at least 12, in particular at least 18, in particular at least 24, in particular at least 32, in particular at least 36, in particular at least 42, in particular at least 48, connecting webs 12, 14. At the same time, it is provided that the lattice structure 10 comprises maximum 80, in particular maximum 70, in particular maximum 60, in particular maximum 50, connecting webs 12, 14.

In principle, the guide system comprises at least one catheter with the aforementioned internal diameter values.

The lattice structure 10 is preferably produced using a physical vapour deposition method (PVD), preferably combined with an etching method. This production variant is particularly suitable for the production of the connecting webs 12, 14, which have a relatively small web width. At least up to a web width of the connecting webs 12, 14 of at the utmost 25 μm, in particular at the utmost 20 μm, in particular at the utmost 15 μm, the combined method consisting of the PVD method, in particular a sputter method, and an etching method has been found to be particularly advantageous.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

LIST OF REFERENCE CHARACTERS

10 Lattice structure
11 First stabilisation web
12 First connecting web
13 Second stabilisation web
14 Second connecting web
15 Cell
16, 16', 16", 16''' Row of stabilisation webs
21 First connector
22 Second connector
23 Third connector
24 Fourth connector
30 Blood vessel
$P_L$ Projection of the longitudinal axis
$P_Q$ Projection of the transverse axis
$b_1$ First web width
$b_2$ Second web width
$l_1$ First web length
$l_2$ Second web length

What is claimed is:

1. A medical device comprising a radially compressible and expandable lattice structure, including at least one closed cell delimited by four webs coupled to one another in one piece, of which at least one web is a stabilisation web with a first web width $b_1$ and at least two further webs are connecting webs with a second web width $b_2$, wherein the connecting webs of the cell are arranged parallel to and opposite one another and are connected to one another by a stabilisation web and wherein a ratio $b_1/b_2$ between the first web width $b_1$ and the second web width $b_2$ is at least 1.2, wherein the lattice structure comprises a plurality of adjacent closed cells, the stabilisation webs of which are connected to one another in an aligned manner such that at least one row of stabilisation webs is formed which is wound in a helical shape around a longitudinal axis of the lattice structure, wherein the connecting webs are substantially S-shaped.

2. The device of claim 1, wherein the ratio $b_1/b_2$ between the first web width $b_1$ and the second web width $b_2$ is at least 1.5.

3. The device of claim 1, wherein two of said four webs are employed as stabilisation webs.

4. The device of claim 1, wherein at least two rows of stabilisation webs are formed, which are connected to one another by respective connecting webs.

5. The device of claim 4, wherein the connecting webs are arranged at regular intervals between the rows of stabilisation webs.

6. The device of claim 1 wherein the connecting webs of adjacent closed cells are arranged parallel to one another.

7. The device of claim 1, wherein the stabilisation webs have a substantially linear course.

8. The device of claim 1, wherein the stabilisation webs have a first web length $l_1$ and the connecting webs have a second web length $l_2$, wherein the first web length $l_1$ and the second web length $l_2$ are different.

9. The device of claim 8, wherein a ratio of the first web length $l_1$ to the second web length $l_2$ ($l_1/l_2$) is at least 1.2.

10. The device of claim 8, wherein a ratio of the first web length $l_1$ to the second web length $l_2$ ($l_1/l_2$) is at least 4.

11. The device according to claim 8, wherein a ratio of the second web length $l_2$ to the first web length $l_1$ ($l_2/l_1$) is at least 1.2.

12. The device according to claim 8, wherein a ratio of the second web length $l_2$ to the first web length $l_1$ ($l_2/l_1$) is at least 4.

13. The device of claim 1, wherein in a circumferential direction, the lattice structure comprises at least 6 connecting webs.

14. The device of claim 1, wherein in a circumferential direction, the lattice structure comprises at the utmost 120 connecting webs.

15. The device of claim 1, wherein the second web width $b_2$ is at the utmost 35 μm.

* * * * *